(12) United States Patent
Elseri

(10) Patent No.: US 9,179,764 B2
(45) Date of Patent: Nov. 10, 2015

(54) TONGUE-MOUNTED CLEANING ARTICLE

(71) Applicant: Adel Elseri, Edmonton (CA)

(72) Inventor: Adel Elseri, Edmonton (CA)

( * ) Notice: Subject to any disclaimer, the term of this patent is extended or adjusted under 35 U.S.C. 154(b) by 259 days.

(21) Appl. No.: 13/838,843

(22) Filed: Mar. 15, 2013

(65) Prior Publication Data

US 2014/0261538 A1 Sep. 18, 2014

(51) Int. Cl.
*A46B 5/04* (2006.01)
*A46B 9/04* (2006.01)
*A46B 9/00* (2006.01)
*A61C 17/00* (2006.01)
*A61H 13/00* (2006.01)

(52) U.S. Cl.
CPC . *A46B 9/005* (2013.01); *A46B 5/04* (2013.01); *A46B 9/04* (2013.01); *A46B 2200/1026* (2013.01); *A61C 17/00* (2013.01); *A61H 13/00* (2013.01)

(58) Field of Classification Search
CPC ........ A61H 13/00; A61C 15/00; A61C 15/02; A61C 17/00; A46B 1/00; A46B 3/005; A46B 3/22; A46B 5/00; A46B 5/04; A46B 9/04; A46B 2200/1026; A46B 2200/1066
USPC .............. 15/104.93, 104.94, 167.1, 187, 188; 433/216; 601/139
See application file for complete search history.

(56) References Cited

U.S. PATENT DOCUMENTS

| | | | |
|---|---|---|---|
| 1,168,998 A | 1/1916 | Brandenburg | |
| 1,894,413 A | 1/1933 | Nenning et al. | |
| 1,946,283 A | 2/1934 | Hoffman et al. | |
| 2,041,262 A * | 5/1936 | Ness | 15/188 |
| 2,077,540 A | 4/1937 | Welker | |
| 2,103,083 A | 12/1937 | Lynch | |
| 2,279,355 A * | 4/1942 | Wilensky | 15/110 |
| D136,631 S | 11/1943 | Bernard et al. | |
| 2,686,325 A | 8/1954 | Silver | |
| 2,966,691 A | 1/1961 | Cameron | |

(Continued)

FOREIGN PATENT DOCUMENTS

DE 10033849 A1 1/2001
DE 10043843 A1 3/2002

(Continued)

OTHER PUBLICATIONS

Deshpande K, Jain A, Sharma R, Prashar S, Jain R. Diabetes and periodontitis. J Indian Soc Periodontol. Oct. 2010;14(4):207-12.
Kelsey JL, Lamster IB. Influence of musculoskeletal conditions on oral health among older adults. Am J Public Health. Jul. 2008;98(7):1177-83. Epub May 29, 2008.

(Continued)

*Primary Examiner* — Mark Spisich
(74) *Attorney, Agent, or Firm* — Parlee McLaws LLP; Kirsten Oates

(57) ABSTRACT

The invention is directed to a tongue-mounted cleaning article for caring for the teeth and gums having an elongated body defining an inner cavity formed in the configuration of the tongue for receiving and accommodating the tongue, and a slot for receiving and accommodating the frenulum on the undersurface of the tongue; an open end sized to permit insertion of tongue; and a closed end being narrower than the open end and configured in the shape of the tip of the tongue, the closed end comprising a plurality of pyramidal protuberances or bristles disposed over a portion or entirety of its surface, wherein the pyramidal protuberances or bristles project outwardly for cleaning the teeth and gums by appropriate movement of the tongue.

13 Claims, 11 Drawing Sheets

(56) References Cited

U.S. PATENT DOCUMENTS

| | | | |
|---|---|---|---|
| 3,043,295 | A | 7/1962 | Ward |
| 3,368,668 | A | 2/1968 | Micciche |
| 3,902,509 | A | 9/1975 | Tundermann et al. |
| 3,905,113 | A | 9/1975 | Jacob |
| 3,959,842 | A | 6/1976 | Alley |
| 4,127,222 | A * | 11/1978 | Adams .................. 223/101 |
| 4,292,705 | A | 10/1981 | Stouffer |
| 4,617,694 | A | 10/1986 | Bori |
| 4,748,709 | A | 6/1988 | Oates |
| 5,068,941 | A | 12/1991 | Dunn |
| 5,107,562 | A | 4/1992 | Dunn |
| 5,213,428 | A | 5/1993 | Salman |
| D339,234 | S | 9/1993 | Vianson |
| 5,392,482 | A | 2/1995 | Drulias et al. |
| 5,440,774 | A | 8/1995 | Cole |
| 5,502,863 | A | 4/1996 | Perkins |
| 5,765,252 | A | 6/1998 | Carr |
| 5,826,599 | A | 10/1998 | Adams |
| 5,875,513 | A | 3/1999 | Reinold |
| 5,909,739 | A | 6/1999 | Masrour-Rad |
| 6,105,587 | A | 8/2000 | Dunn |
| 6,722,805 | B1 | 4/2004 | Skinner |
| 6,808,068 | B2 | 10/2004 | Abada |
| RE39,185 | E | 7/2006 | Noe et al. |
| D533,352 | S | 12/2006 | Bernini |
| D576,796 | S | 9/2008 | Roman |
| 7,895,695 | B2 | 3/2011 | Bernini et al. |
| 2005/0260027 | A1 | 11/2005 | Levy |
| 2012/0048287 | A1* | 3/2012 | White ..................... 132/200 |

FOREIGN PATENT DOCUMENTS

| | | |
|---|---|---|
| DE | 20219863 U1 | 4/2003 |
| DE | 2004105633 A1 | 12/2004 |
| EP | 0252710 A1 | 1/1988 |

OTHER PUBLICATIONS

Komiyama EY, Back-Brito GN, Balducci I, Koga-Ito CY. Evaluation of alternative methods for the disinfection of toothbrushes. Braz Oral Res. Jan.-Mar. 2010;24(1):28-33.

Li X, Kolltveit KM, Tronstad L, Olsen I. Systemic diseases caused by oral infection. Clin Microbiol Rev. Oct. 2002; 13 (4):547-58.

Lockhart PB, Brennan MT, Thornhill M, Michalowicz BS, Noll J, Bahrani-Mougeot FK, Sasser HC. Poor oral hygiene as a risk factor for infective endocarditis-related bacteremia. J Am Dent Assoc. Oct. 2009;140(10):1238-44.

Michalowicz BS, Hodges JS, Lussky RC, Bada H, Rawson T, Buttross LS, Chiriboga C, Diangelis AJ, Novak MJ, Buchanan W, Mitchell DA, Papapanou PN. Treatment of periodontal disease and the risk of preterm birth. N Engl J Med. Nov. 2, 2006;355(18):1885-94.

De Oliveira C, Watt R, Hamer, M. Toothbrushing, inflammation, and risk of cardiovascular disease: results from Scottish Health Survey. BMJ. May 27, 2010;340:c2451. doi: 10.1136/bmj.c2451.

Raghavendran K, Mylotte JM, Scannapieco FA. Nursing home-associated pneumonia, hospital-acquired pneumonia and ventilator-associated pneumonia: the contribution of dental biofilms and periodontal inflammation. Periodontol 2000. 2007;44:164-77.

Rawls HR, Mkwayi-Tulloch NJ, Casella R, Cosgrove R. The measurement of toothbrush wear. J Dent Res. Dec. 1989;68(12):1781-5.

Sato S, Ito IY, Lara Ehg, Panzeri H. Bacterial survival rate on toothbrushes and their decontamination with antimicrobial solutions. J Appl Oral Sci 2004:12(2):99-103.

Spahr A, Klein E, Khuseyinova N, Boeckh C, Muche R, Kunze M, Rothenbacher D, Pezeshki G, Hoffmeister A, Koenig W. Periodontal infections and coronary heart disease: role of periodontal bacteria and importance of total pathogen burden in the Coronary Event and Periodontal Disease (Corodont) study. Arch Intern Med. Mar. 13, 2006;166 (5):554-9.

* cited by examiner

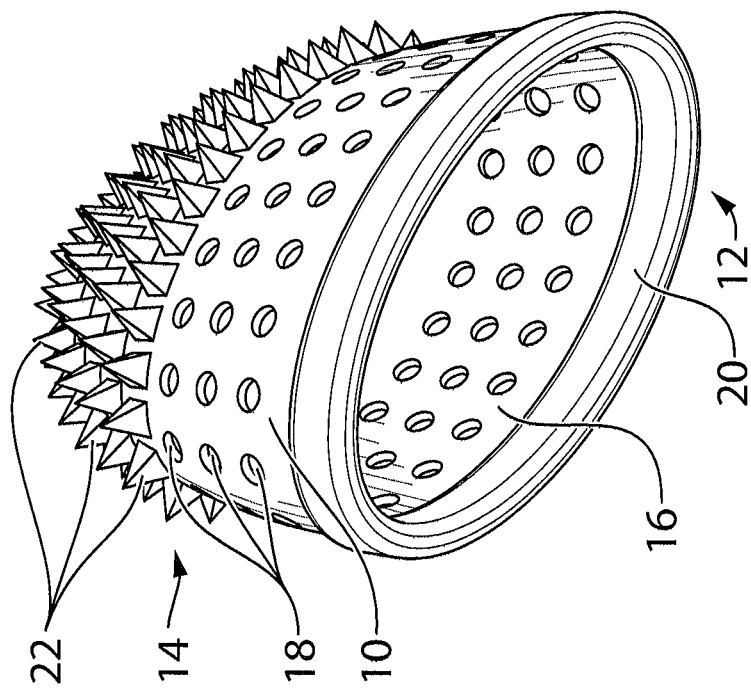
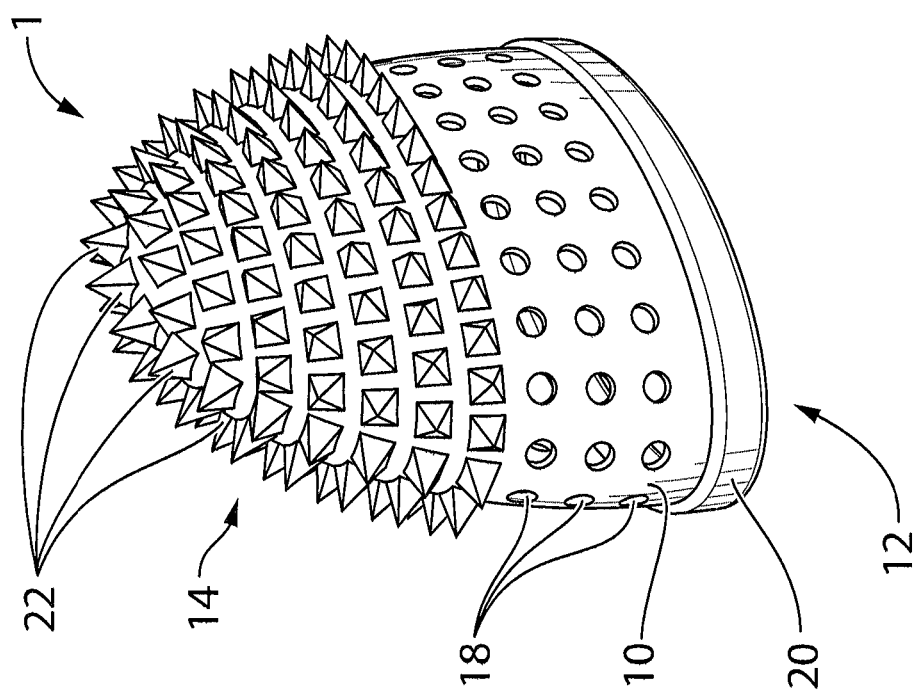
FIG.1B
FIG.1A

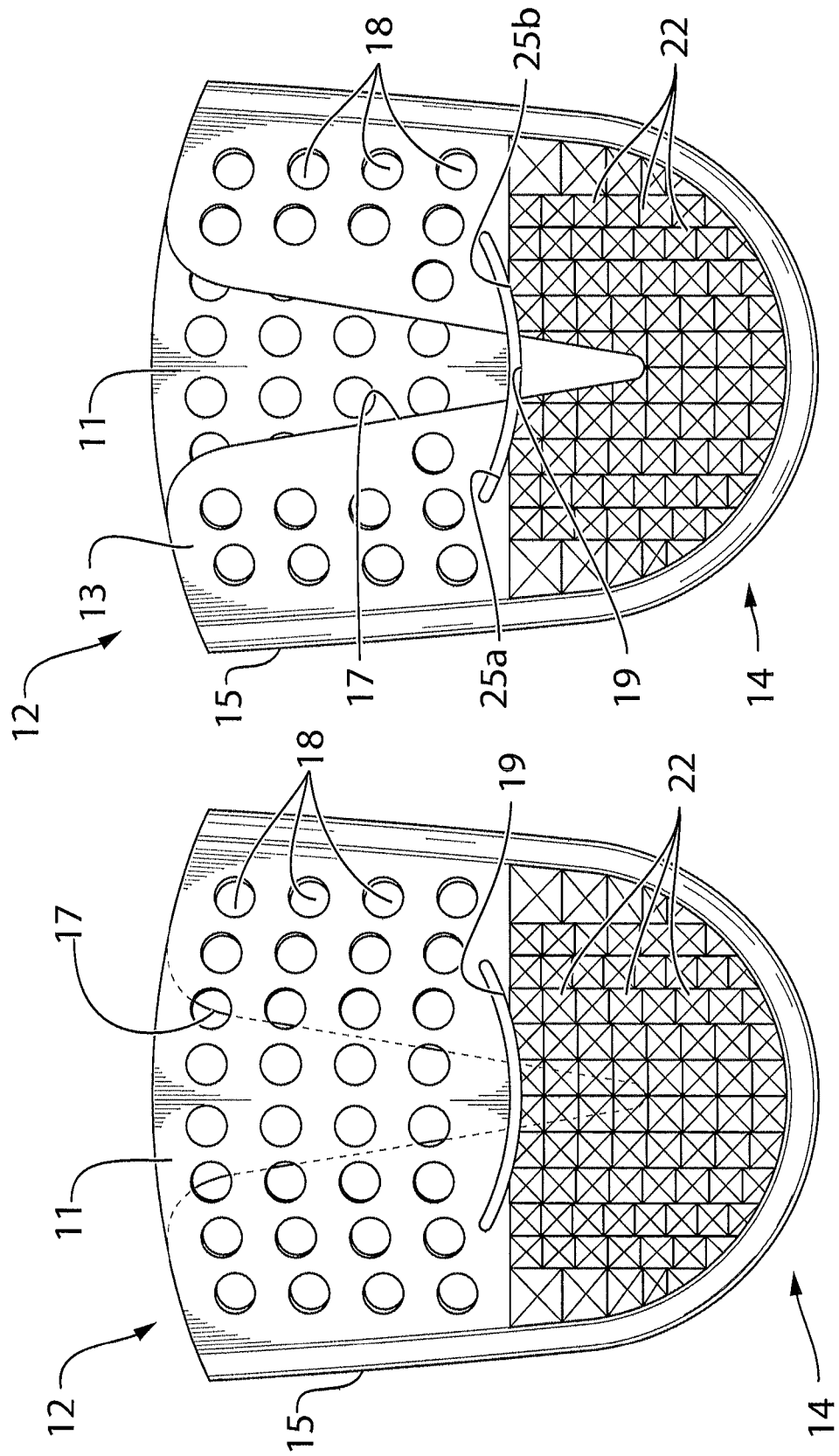

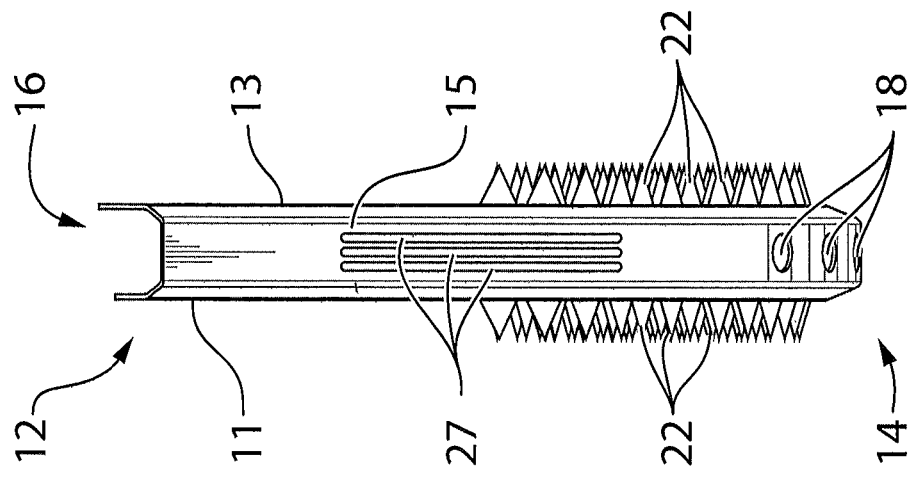
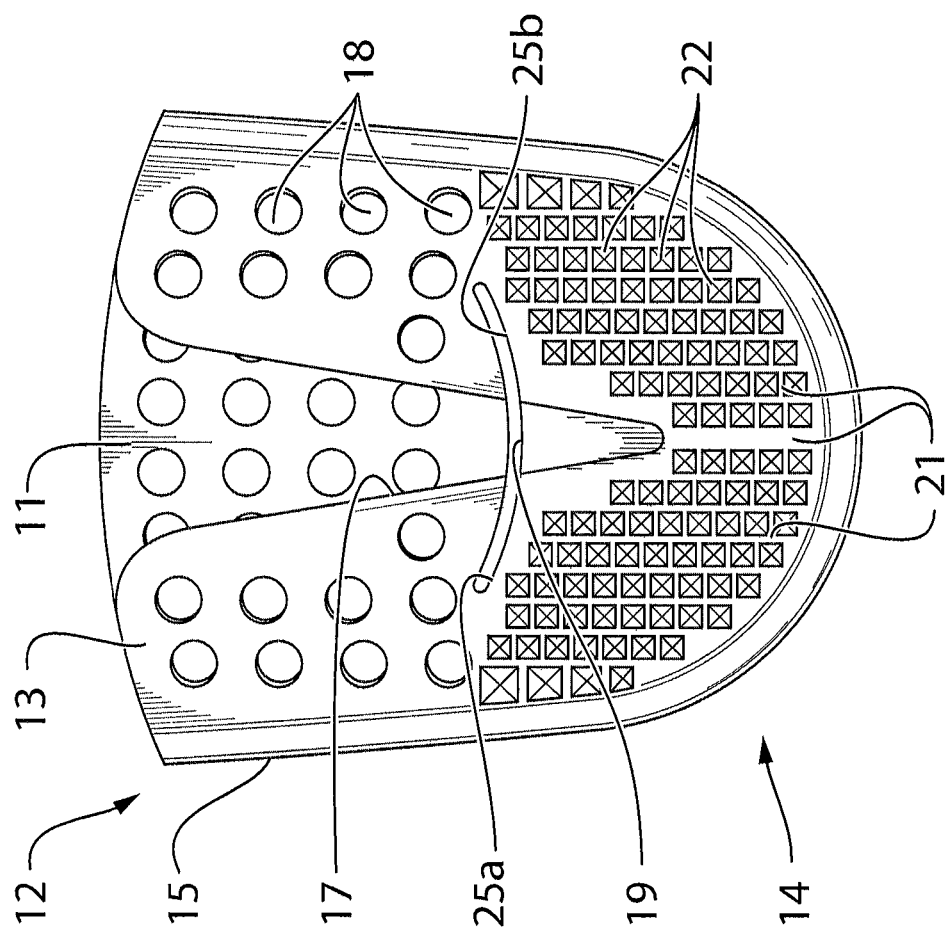

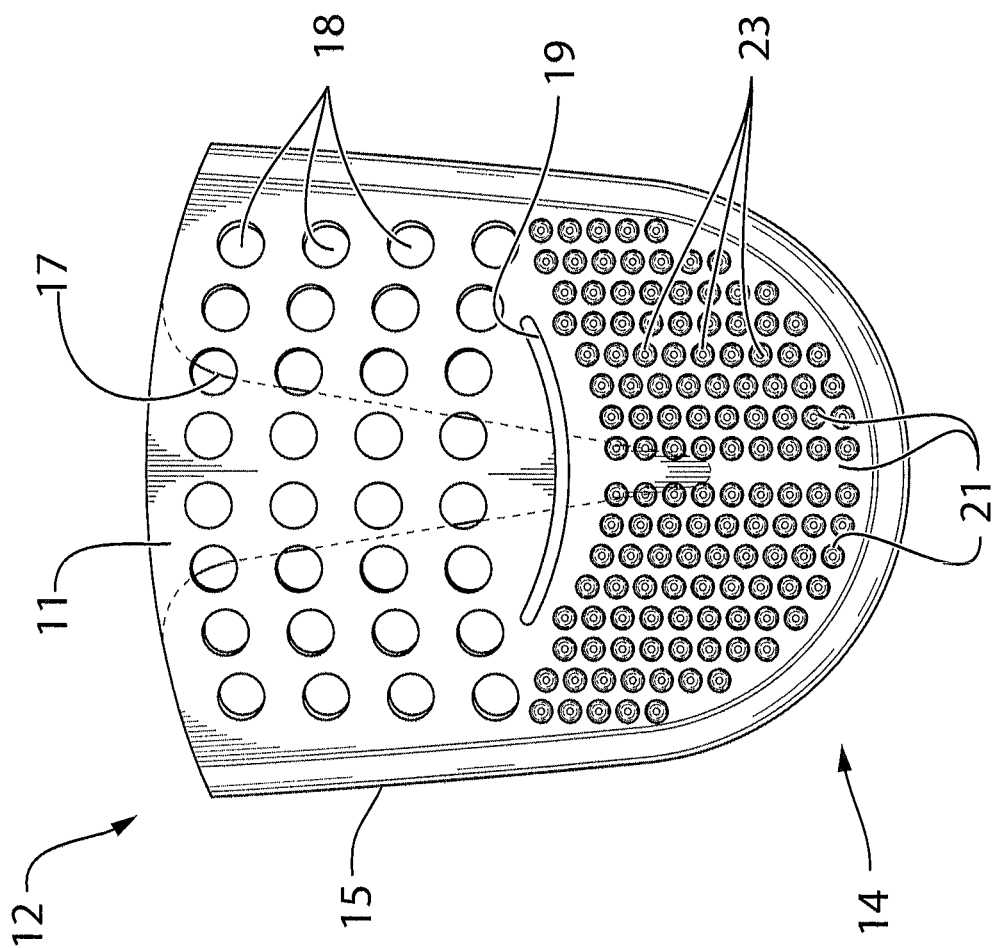

TONGUE-MOUNTED CLEANING ARTICLE

FIELD OF THE INVENTION

The invention relates to a tongue-mounted cleaning article for caring for the teeth and gums.

BACKGROUND OF THE INVENTION

It has been recently recognized that poor oral hygiene may contribute to various systemic diseases. Oral bacteria are normally present in the mouth, and include strains of streptococci, lactobacilli, staphylococci, corynebacteria, and various anaerobes, particularly bacteroides. Although such bacteria can be beneficial to one's health, some bacteria can be harmful and cause serious illnesses; for example, *Streptococcus mutans* converts sugars and starches into acids and enzymes which dissolve tooth enamel, and causes pneumonia, sinusitis and meningitis.

Bacteria, acid, food debris, and saliva combine in the mouth to form a sticky substance known as plaque which adheres to tooth, tongue and gum surfaces within twenty minutes after eating. Plaque accumulation causes inflammation of the gums or gingivitis, and can progress to destruction of the ligaments and bone that support the teeth (i.e., periodontitis). Plaque which is not removed from the teeth mineralizes into calculus which can cause halitosis, receding gums, and chronically inflamed gingiva.

Further, the bacteria in plaque and calculus can disseminate from the mouth into other areas of the body such as the bloodstream and lungs. Three pathways linking oral infections to systemic effects have been proposed (Li et al., 2000). Bacteria may enter the bloodstream and circulate throughout the body to settle at a particular site, may produce exotoxins which are harmful to the body, and/or may form immuno-complexes which may promote inflammatory reactions. Systemic diseases associated with oral infection include cardiovascular diseases, coronary heart disease, infective endocarditis, bacterial pneumonia, lung disease, osteoporosis, diabetes mellitus, and low birth weight (De Oliveira et al., 2010; Deshpande et al., 2010; Kelsey et al., 2008; Lockhart et al., 2009; Michalowicz et al., 2006; Raghavendran et al., 2007; Spahr et al., 2006).

Prevention of plaque and calculus may be achieved by regular professional cleaning and diligence in brushing and flossing. However, many people do not make a regular practice of visiting their dentists or caring for their teeth. Many dentists recommend professional cleaning every six months. However, peridontal scalers or ultrasonic tools for removing deposits from teeth often cause discomfort, such that patients generally defer or avoid their appointments. Further, patients who have lower incomes (e.g., seniors) or lack dental insurance have less access to oral care services.

Dental professionals recommend brushing twice a day or after meals, and flossing daily. However, most people do not have the inclination or time. Those with sensitive teeth or irritated gums may avoid proper care of the affected areas. Certain pharmaceutical drugs (e.g., phenytoin, cyclosporine, calcium channel blockers such as nifedipine and amlodipine) cause gingival hyperplasia, which facilitates invasion of bacteria into the gums to cause painful irritation or inflammation (Lowenthal et al., 2001). As a result, those afflicted are less likely to brush, making gingivitis more likely to develop or worsen.

Various articles have been developed to facilitate care for the teeth and gums, including bristled manual or electric toothbrushes, dental floss, and interdental cleaners. Manual toothbrushes require effort, skill and brushing force which can damage teeth if overly vigorous. In contrast, electric toothbrushes require minimal skill, are effective for people with arthritis or other physical limitations, and are ergonomic for a comfortable grasp. However, electric toothbrushes are bulky, more expensive than manual toothbrushes, difficult to maneuver, require battery replacement or recharging, necessitate the purchase of replacement heads every three to four months, and generally do not provide soft or extra-soft bristles for very sensitive teeth.

After multiple uses, bacteria tend to accumulate in toothbrush bristles which are difficult to disinfect thoroughly without the use of antimicrobial solutions or decontamination techniques which tend to be unavailable to consumers (Komiyama et al., 2010; Sato et al., 2004). The ability of brushes to remove plaque has been found to be significantly reduced after as little as ten weeks (Rawls et al., 1989). Since splaying of bristles increases with use, cleaning efficiency subsequently decreases.

Dental floss removes unwanted debris which collects between the teeth and which is not always removed by a toothbrush. If used improperly, dental floss can scrape the insides of the teeth, rupture gum tissue, and cause unnecessary bleeding. There may be areas where dental floss becomes stuck due to tightly spaced teeth, or frays due to rough or sharp areas found on either the surface of a tooth or a dental restoration such as a filling, crown or veneer. Alternatively, a flossing handle, electric or pre-threaded flosser, or interdental cleaner such as a dental pick or stick may be used to clean between teeth. However, all flossing methods require dexterity and patience. A water pick or oral irrigator aims a stream of water at the teeth and may help to remove large particles, but is not generally considered a substitute for brushing and flossing.

A problem shared by the above cleaning articles is that they are cumbersome, bulky or inconvenient to carry such that many forego carrying a toothbrush and/or floss with them, leading to poor oral hygiene. There is often a lack of opportunity to brush or floss during work or social activities, or facilities available to brush or floss in privacy.

Accordingly, there is thus a need in the art for improved articles and methods for caring for the teeth and gums.

SUMMARY OF THE INVENTION

The present invention relates to a tongue-mounted cleaning article for caring for the teeth and gums. In one aspect, the invention comprises a tongue-mounted cleaning article for caring for the teeth and gums comprising:

a) an elongated body defining an inner cavity formed in the configuration of the tongue for receiving and accommodating the tongue, and a slot for receiving and accommodating the frenulum on the undersurface of the tongue;

b) an open end sized to permit insertion of tongue; and c) a closed end being narrower than the open end and configured in the shape of the tip of the tongue, the closed end comprising a plurality of pyramidal protuberances or bristles disposed over a portion or entirety of its surface, wherein the pyramidal protuberances or bristles project outwardly for cleaning the teeth and gums by appropriate movement of the tongue.

In one embodiment, the body has a plurality of apertures therethrough.

In one embodiment, the body comprises a top side, a bottom side, and an edge. In one embodiment, the apertures are positioned on at least the top side and the bottom side. In one embodiment, at least one aperture is positioned on the edge at the tip of the closed end.

In one embodiment, the article further comprises one or more weakening structures. In one embodiment, the one or more weakening structures are positioned on one or more of the top side, the bottom side, or the edge.

In one embodiment, the weakening structure comprises one or more top slots defined by the top side.

In one embodiment, the weakening structure comprises one or more pairs of bottom slots defined by the bottom side.

In one embodiment, the weakening structure comprises one or more edge slots defined by the edge.

In one embodiment, the weakening structure comprises one or more spacings between adjacent pyramidal protuberances or bristles.

In one embodiment, each pyramidal protuberance comprises a polygonal base and a plurality of triangular faces which converge at an apex, the bases of the faces of each pyramidal protuberance directly abutting the bases of the faces of adjacent pyramidal protuberances to define channels between the protuberances.

In one embodiment, each pyramidal protuberance comprises at least three triangular faces. In one embodiment, each pyramidal protuberance comprises four triangular faces.

In one embodiment, one or more abrasive pads are provided on one or more of the triangular faces.

In one embodiment, the article comprises an elastomer.

In one embodiment, the article further comprises a coating on one or both of the body and the protuberances or the bristles, the coating being at least one of antibacterial agent, an antibiotic, an anti-inflammatory agent, a tissue ingrowth promoter, a dentifrice, a tooth whitening agent, a breath freshener, a flavoring, a polishing agent, or combinations thereof.

In another aspect, the invention comprises a method of cleaning the teeth and gums by appropriate movement of the tongue, the method comprising the steps of: providing the above article; mounting the article on the tongue; and manipulating the article with the tongue to allow the pyramidal protuberances or bristles to clean the teeth and gums.

Additional aspects and advantages of the present invention will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described by way of an exemplary embodiment with reference to the accompanying simplified, diagrammatic, not-to-scale drawings. In the drawings:

FIG. 1A is a front view of one embodiment of the tongue-mounted cleaning article of the present invention.

FIG. 1B is a rear view of the tongue-mounted cleaning article of FIG. 1A.

FIG. 6A is a top view of one embodiment of the tongue-mounted cleaning article of the present invention.

FIG. 6B is a bottom view of the tongue-mounted cleaning article of FIG. 6A.

FIG. 7B is a bottom view of the tongue-mounted cleaning article of FIG. 7A.

FIG. 7C is a side view of the tongue-mounted cleaning article of FIG. 7A.

FIG. 9A is a top view of one embodiment of the tongue-mounted cleaning article of the present invention.

DETAILED DESCRIPTION OF PREFERRED EMBODIMENTS

Figure 2B:
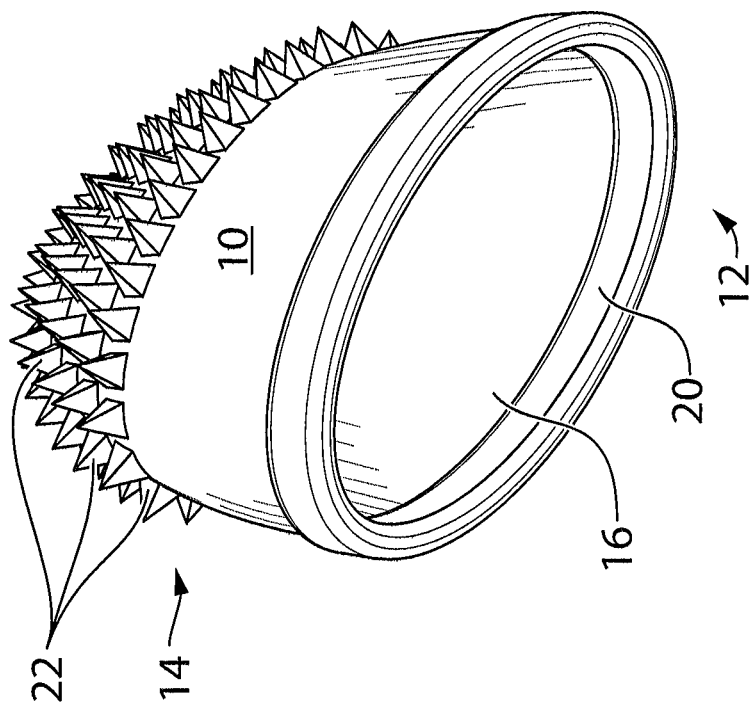
FIG. 2B is a rear view of the tongue-mounted cleaning article of FIG. 2A.

The present invention relates to a tongue-mounted cleaning article for caring for the teeth and gums.

Before the present invention is described in further detail, it is to be understood that the invention is not limited to the particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

It must be noted that as used herein and in the appended claims, the singular forms "a", "an", and "the" include plural referents unless the context clearly dictates otherwise.

The present invention comprises a tongue-mounted cleaning article (1). The cleaning article (1) is configured to be engaged by the tongue, and which when worn, will operate to clean the teeth and gums of plaque and debris, and can also be used in the manner in which a typical toothbrush is commonly employed.

In one embodiment, the invention comprises a tongue-mounted cleaning article for caring for the teeth and gums comprising:

a) an elongated body defining an inner cavity formed in the configuration of the tongue for receiving and accommodating the tongue, and a slot for receiving and accommodating the frenulum on the undersurface of the tongue;

b) an open end sized to permit insertion of tongue; and c) a closed end being narrower than the open end and configured in the shape of the tip of the tongue, the closed end comprising a plurality of pyramidal protuberances or bristles disposed over a portion or entirety of its surface, wherein the pyramidal protuberances or bristles project outwardly for cleaning the teeth and gums by appropriate movement of the tongue.

The invention will now be described having reference to the accompanying figures. The article (1) is shown generally in the Figures to include an elongated body (10), an open end (12), and a closed end (14). The body (10) is hollow and defines an inner cavity (16) for receiving and accommodating the tongue. The inner cavity (16) is formed in the general configuration of the tongue to provide a comfortable fit.

In one embodiment, the body (10) has a top side (11) and a bottom side (13) which are joined by an edge (15). The bottom side (13) defines a centered slot (17) for accommodating the frenulum. The frenulum is the vertical fold of mucous membrane under the tongue and anchors the tongue to the floor of the mouth. In one embodiment, the slot (17) is substantially V-shaped. The slot (17) starts proximal to the closed end (14) and broadens in the direction of the open end (12) into a V shape.

In one embodiment, the body (10) may have perforations or apertures (18). A mucous membrane covers the tongue. The dorsum of the tongue contains projections of the mucosa known as papillae which contain the taste buds and serous glands which secrete some of the fluids in saliva. In one embodiment, perforations or apertures (18) pass through the body (10) to allow the passage of such secretions in order to moisten and lubricate the mouth during the cleaning process (FIGS. 1A-B, 6A-B, 7A-C, 8A-B, 9A-C). In addition, the apertures (18) provide suction to prevent slippage and to maintain the article (1) on the tongue.

It is contemplated that the number (density), size (diameter), shape, and positioning of the apertures (18) for an embodiment of the article (1) may vary. In one embodiment, the diameter of the apertures (18) may be in the range of between about 0.3 mm to about 3.0 mm, preferably between about 0.5 mm to about 2.0 mm. The number of apertures included may range from 1 to 100, more preferably 2 to 50.

In one embodiment, the apertures (18) may be micro-perforations having a diameter in the range of between about one micron (1μ) to about five hundred (500μ) microns, preferably between about fifty microns (50μ) to about one hundred fifty (150μ) microns. The number of micro-perforations included may range from 1 to 1,000, more preferably 2 to 150.

It is contemplated that the number and size of the apertures (18) or micro-perforations per article (1) may vary without departing from the scope and spirit of the present invention. Apertures (18) and microperforations may be made using a number of methods known to those skilled in the art, including but not limited to laser perforation.

In one embodiment, the apertures (18) are positioned on one or more of the top side (11), bottom side (13), and edge (15) (FIGS. 6A-B, 7A-C, 8A-B, 9A-C). In one embodiment, the apertures (18) are positioned on the edge (15). In one embodiment, the apertures (18) are positioned on the edge (15) at the tip of the closed end (14) (FIGS. 7C, 8A-B, 9C). In one embodiment, at least one aperture (18) is positioned at the tip of the closed end (14). Having at least one aperture (18) at the tip of the closed end (14) provides suction to prevent slippage and to maintain the article (1) on the tongue.

Figure 2A:
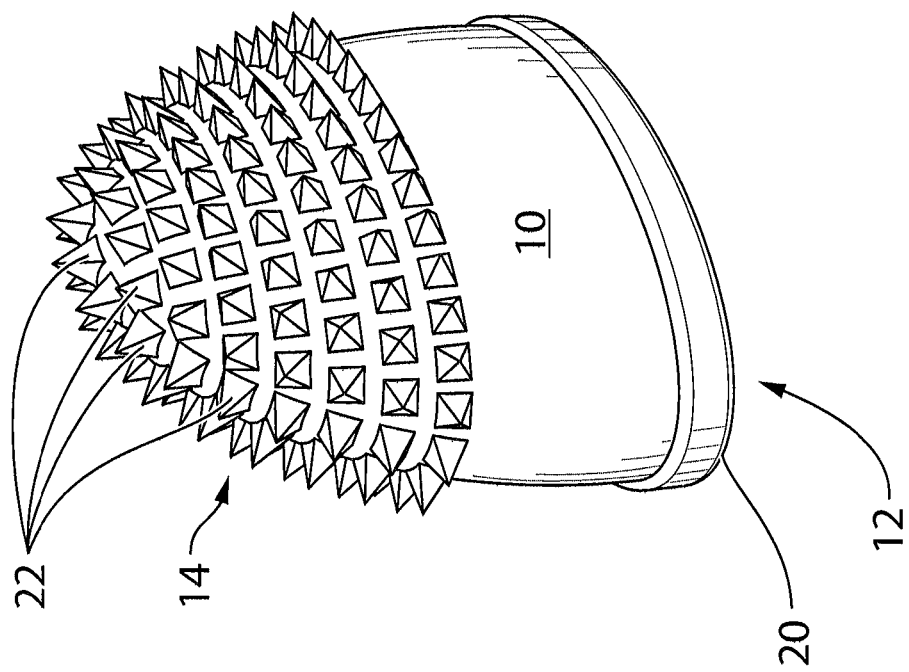
FIG. 2A is a front view of one embodiment of the tongue-mounted cleaning article of the present invention.

In one embodiment, the body (10) may not have perforations or apertures (18) to minimize manufacturing costs (FIGS. 2A-B).

As is well known, the tongue is typically of greater cross sectional area at its rear portion where it is attached within the oral cavity than the cross sectional area of the tongue adjacent its apex or tip. Accordingly, the open end (12) is large enough to permit insertion of the tongue. In one embodiment, the open end (12) is reinforced with an annular elastic member (20) which is used to attach or detach the article (1) from the tongue. In one embodiment, the elastic member (20) has a thickness greater than that of the body (10). The elastic member (20) is capable of contracting or widening to snugly encircle and secure the tongue so as to prevent the article (1) from slipping off the tongue or being accidentally swallowed.

The closed end (14) is narrower than the open end (12), and is configured in the shape of the tip of the tongue. The closed end (14) thus receives and accommodates the tip of the tongue.

The surface structure of the closed end (14) comprises protuberances in the form of pyramidal protuberances (22) or bristles (23). In one embodiment, the protuberances (22) are pyramidal-shaped. A plurality of pyramidal protuberances (22) project outwardly from the exterior surface of the closed end (14). In one embodiment, the pyramidal protuberances (22) are disposed over the entirety of the surface of the closed end (14). In one embodiment, the pyramidal protuberances (22) are disposed over at least a portion of the surface of the closed end (14). In one embodiment, the pyramidal protuberances (22) are evenly distributed over the entirety of the surface of the closed end (14). In one embodiment, the pyramidal protuberances (22) are evenly distributed over at least a portion of the surface of the closed end (14).

In one embodiment, the pyramidal protuberances (22) are disposed or evenly distributed over the surface of the closed end (14) on at least one or more of the top side (11), bottom side (13), and edge (15). In one embodiment, the pyramidal protuberances (22) are disposed or evenly distributed over the surface of the closed end (14) on the top side (11) and bottom side (13) (FIGS. 6A-B, 7A-C, 8A-B).

In one embodiment, the pyramidal protuberances (22) generally comprise a polygonal base (24) and triangular faces (26) which converge at a common apex (28). In one embodiment, the pyramidal protuberances (22) comprise four triangular faces (26). While the Figures illustrate square pyramids, it will be appreciated by those skilled in the art that triangular pyramids, pentagonal pyramids and the like are included within the scope of the invention.

In one embodiment, one or more abrasive elements (30) may be provided on one or more of the triangular faces (26) of the pyramidal protuberance (22) to remove plaque or debris by frictional contact or abrasion. In one embodiment, the abrasive element (30) comprises a pad which may be integral or mounted to the triangular face (26). The pad has a thickness ranging from about 0.5 mm to about 3 mm, preferably about 1 mm to about 2 mm. The abrasive element (30) may be formed of various abrasive materials. As used herein, the term "abrasive" means capable of abrading or scraping a surface. Suitable abrasive materials may include, but are not limited to, rubber, latex, nylon, loofah, felt and the like. The abrasive elements (30) are particularly useful where special difficulty is found in the removal of forms of hardened plaque such as calculus or tartar, or sticky debris such as for example, toffee, caramel, and dried fruit.

Figure 3B:
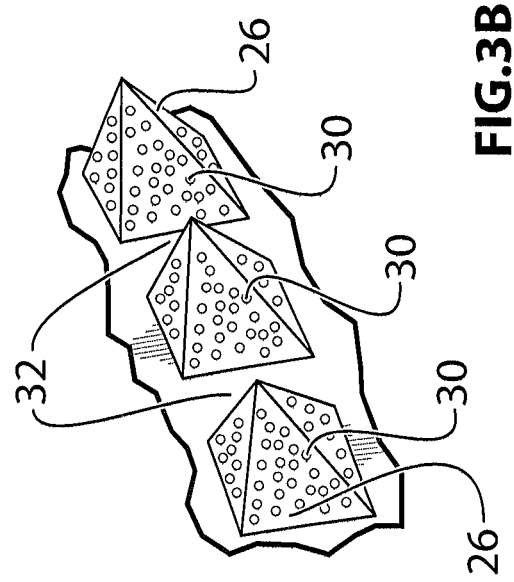
FIG. 3B is an enlarged view of the pyramidal protuberances having abrasive elements.
Figure 3A:
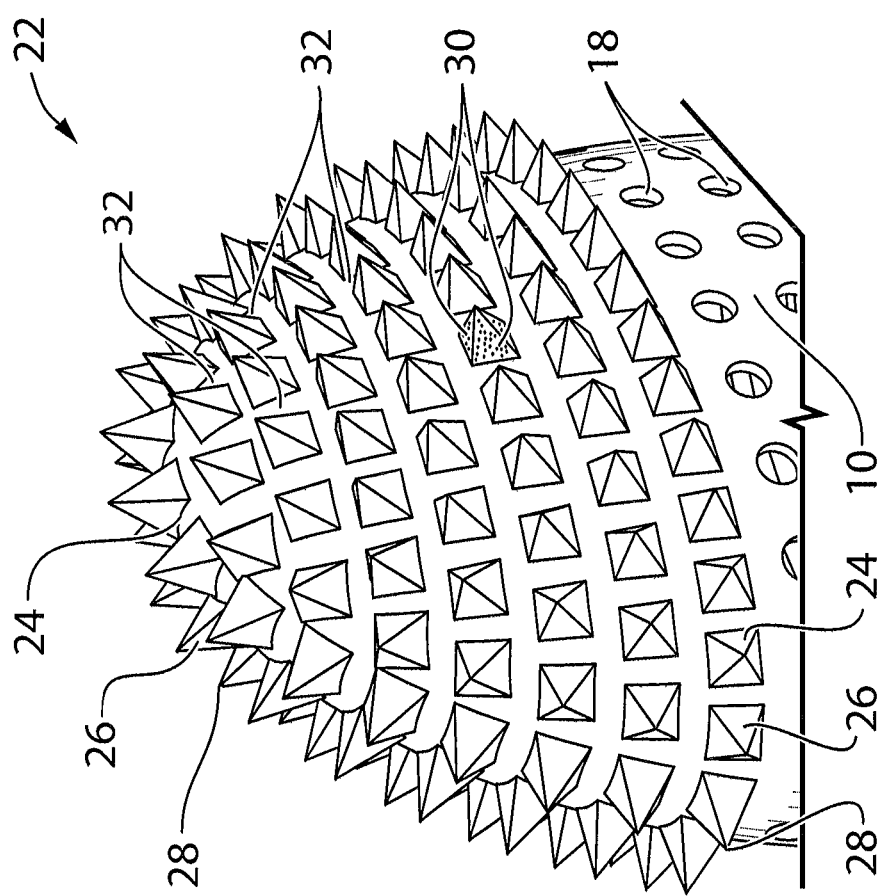
FIG. 3A is an enlarged view of one embodiment of the tongue-mounted cleaning article, showing the detail of the pyramidal protuberances.

It is contemplated that the number (density), size, shape and positioning of the abrasive elements (30) may vary. Such factors relating to the abrasive elements (30) are dictated by the dimensions of the faces (26). While FIGS. 3A and 3B illustrate circular or oval-shaped abrasive elements (30), it will be appreciated by those skilled in the art that other shapes such as for example, triangular, square, rectangular and the like, are included within the scope of the invention. While FIG. 3A illustrates abrasive elements (30) on a representative pyramidal protuberance (22) on one embodiment of the article (1), it will be appreciated by those skilled in the art that a plurality of pyramidal protuberances (22) may also include abrasive elements (30) on their faces (26) as shown for example, in FIG. 3B.

In one embodiment, the pyramidal protuberances (22) are of the same size. It is particularly preferred to have the pyramidal protuberances (22) the same size since this lends itself to the possibility of making pyramidal protuberances (22) of identical structure, thereby simplifying and reducing manufacturing costs. However, if desired, the pyramidal protuberances (22) may be of different sizes to clean the different surfaces of the teeth and gums as efficiently as possible. As an example, the pyramidal protuberances (22) may be consistent in size and on a flat plane in order to clean flat areas such as the front and back faces of the teeth. Wider based pyramidal protuberances (22) may be included to clean the deeper pits of the molars. Pyramidal protuberances (22) on the sides of the article (1) may be positioned on an angle to sweep and stimulate the gums or to dig in and clean in between the spaces of the teeth. Pyramidal protuberances (22) at the tip of the article (1) may be larger in size than the pyramidal protuberances (22) at the sides of the article (1) to extend the reach to particular areas within the mouth.

The dimensions of the pyramidal protuberances (22) are not essential to the invention and may be increased or decreased as may be required to satisfy any particular design objectives. If half of a pyramidal protuberance (22) is imagined as a right triangle with the hypotenuse being the length, possible dimensions for that triangle would range from about 2 mm to about 8 mm in length; about 1 mm to about 5 mm in height; and about 1 mm to about 5 mm in width. In one embodiment, the pyramidal protuberances (22) range from about 1 mm to about 8 mm in length, preferably about 4 mm to about 6 mm; about 1 mm to about 5 mm in height, preferably about 2 mm to about 4 mm; and about 1 mm to about 5 mm in width, preferably about 2 mm to about 4 mm. In one embodiment, the pyramidal protuberances (22) are about 1 mm in length, about 2 mm in height, and about 1 mm in width.

The pyramidal protuberances (22) are arranged as closely together as is practicable to maximize the contacting surface and to ensure that any plaque or debris cleared from the teeth or gums will remain entrapped within the protuberances (22). In one embodiment, each pyramidal protuberance (22) is disposed to directly abut an adjacent pyramidal protuberance (22) to define a channel (32) between the protuberances (22). As shown in FIGS. 3A and 6A-B, the bases (24) of the faces (26) of each pyramidal protuberance (22) directly abut the bases (24) of the faces (26) of adjacent pyramidal protuberances (22) to form the channels (32). The channels (32) thus entrap or collect plaque or debris cleared from the teeth or gums.

Having protuberances (22) in the shape of pyramids and covering at least a portion or the entirety of the surface of the closed end (14) maximizes the contacting surface, such that all areas of the mouth can be reached for cleaning, including the front and back of the upper and lower central and lateral incisors, canine teeth, premolars and molars; the crevices between the teeth; the floor and roof of the mouth; and the insides of the cheeks.

Figure 9C:
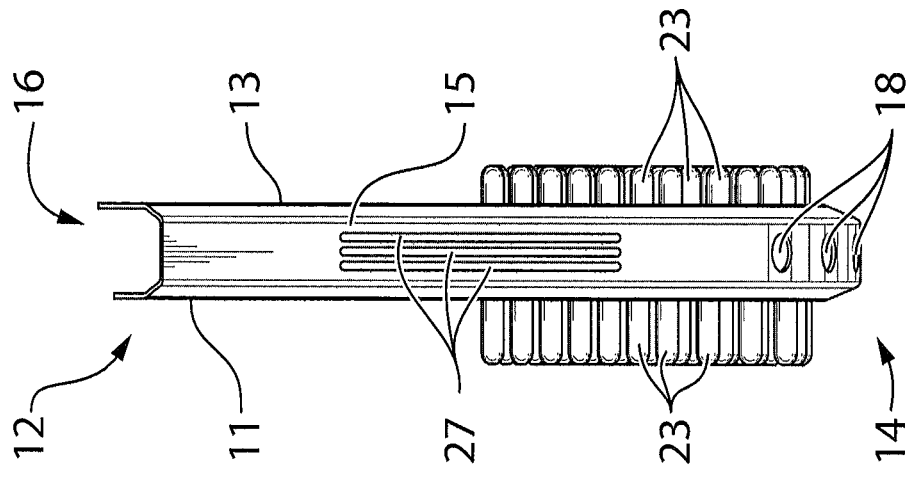
FIG. 9C is a side view of the tongue-mounted cleaning article of FIG. 9A.
Figure 9B:
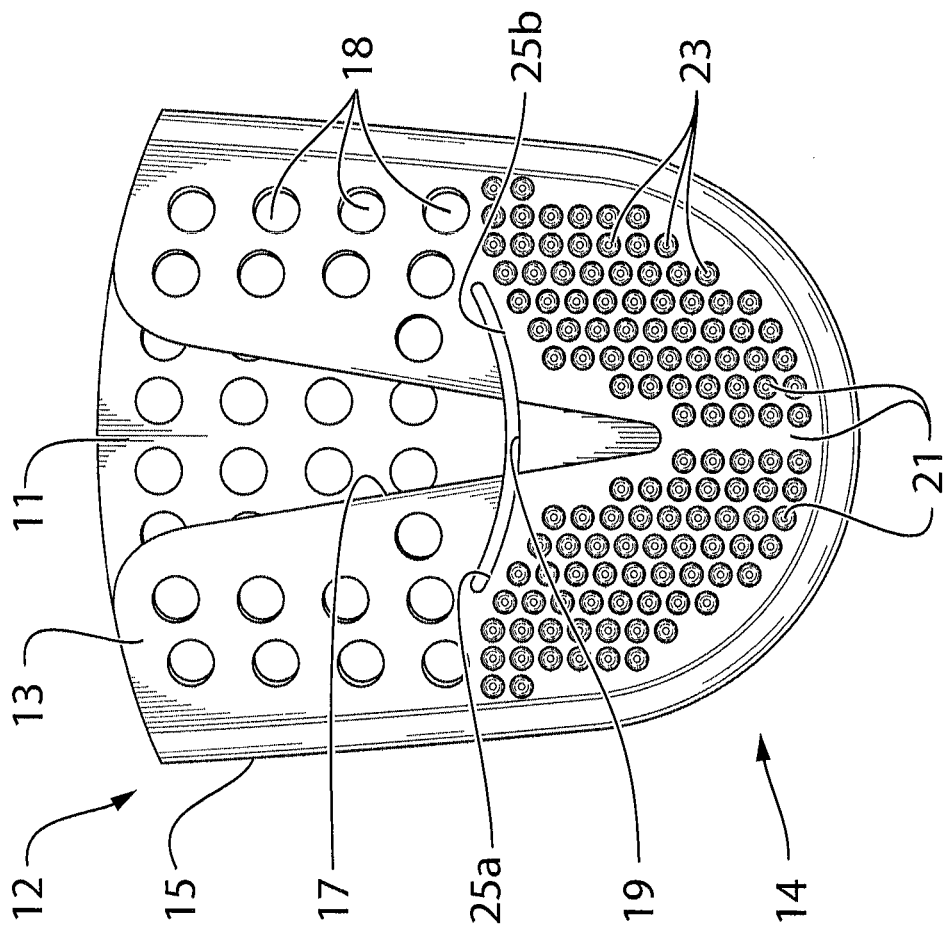
FIG. 9B is a bottom view of the tongue-mounted cleaning article of FIG. 9A.

In one embodiment, the protuberances comprise bristles or filaments (23) which project outwardly from the exterior surface of the closed end (14) (FIGS. 9A-C). In one embodiment, the bristles (23) are disposed or evenly distributed over the surface of the closed end (14) on at least one or more of the top side (11), bottom side (13), and edge (15). In one embodiment, the bristles (23) are disposed or evenly distributed over the surface of the closed end (14) on the top side (11) and bottom side (13) (FIGS. 9A-C).

The bristles (23) are either formed integrally with the article (1) or imbedded in the closed end (14). When imbedded, the bristles (23) have anchored ends firmly secured to the closed end (14) and opposite exposed ends which project outwardly from the surface of the closed end (14) (FIG. 9C). The closed end (14) thus maintains the bristles (23) mounted in an orientation perpendicular to the surface of the closed end (14). The bristles (23) may take a configuration known to one of ordinary skill in the art such as a configuration used on any known toothbrush. The bristles (23) may be formed of nylon or other suitable plastic. The bristles (23) may have the same length or vary in length. In one embodiment, the bristles (23) disposed or evenly distributed over the surface of the closed end (14) on the top side (11) have a greater length than the bristles (23) disposed or evenly distributed over the surface of the closed end (14) on the bottom side (13) (FIG. 9C). In one embodiment, the bristles (23) range in length from about 1 mm to about 8 mm.

The article (1) may be disposed over at least a portion of the tongue and may be positioned to closely fit at least partially over the tongue and over at least an anterior portion of the tongue. The user may position his tongue (T) through the open end (12) into the body (10), and advance the tongue so its tip fits snugly within the closed end (14). The article (1) may be adjusted by the user to cover a greater or lesser portion of the tongue depending upon the desired fit and comfort so long as the covered portion of the tongue is sufficient for the article (1) to be secured over the tongue.

The dimensions of the article (1) are not essential to the invention and are dictated by the size of the tongue. The average length of the adult or adolescent human tongue from the oropharynx to the tip is about 10 cm. The dimensions of the article (1) may be increased or decreased as may be required to satisfy any particular design objectives. In one embodiment, the article (1) has a length ranging from about 2 cm to about 6 cm, preferably from about 3 cm to about 5 cm, and a width ranging from about 2 cm to about 4 cm, preferably from about 3 cm to about 5 cm. In one embodiment, the article (1) has an edge (15) having a width ranging from about 0.5 cm to about 1 cm, preferably from about 0.6 cm to about 0.8 cm.

The article (1) may be formed of various flexible, elastic materials. As used herein, the term "flexible" means capable of bending without breaking. Rigid materials are avoided since they may break or be abrasive to the teeth and gums. In one embodiment, the article (1) comprises flexible, elastomeric materials which can widen or contract to accommodate any size of tongue. As used herein, the term "elastomer" means a material which exhibits the property of elasticity, namely the ability to deform when a stress is applied and to recover its original form (i.e., length, volume, shape, etc.) spontaneously when the stress is removed. Elastomers typically have a low Young's modulus (i.e., the ratio of tensile stress to tensile strain, expressed in units of pressure), and a high yield strain (i.e., the stress at which a material begins to deform plastically, expressed in units of pressure). Suitable elastomeric materials include, but are not limited to, polyisoprene or natural rubber, latex, polyurethane, polyethylene, polyvinyl chloride, and nylon. Preferably, the elastomeric materials are non-toxic, bioinert and impervious to saliva.

In one embodiment, the article (1) is provided with one or more weakening structures to facilitate the flexibility or bending of the article (1) during use. It is contemplated that the number, position and configuration of the weakening structures may vary without departing from the scope and spirit of the present invention. The weakening structure may be positioned anywhere on the article (1) as required. In one embodiment, the weakening structure is positioned on one or more of the top side (11), bottom side (13), and edge (15) of the article (1).

In one embodiment, the weakening structure comprises one or more top slots (19). In one embodiment, the top slot (19) is curved to match the contour of the closed end (14). In one embodiment, the top slot (19) is defined by the top side (11). In one embodiment, the top slot (19) is defined by the top side (11) and is positioned between the apertures (18) and pyramidal protuberances (22) (FIGS. 6A, 7A, 8A) or bristles (23) (FIG. 9A).

In one embodiment, the weakening structure comprises one or more pairs of bottom slots (25a, 25b) which intersect the centered slot (17) that accommodates the frenulum (FIGS. 6B, 7B, 8B, 9B). In one embodiment, the bottom slots (25a, 25b) are curved to match the contour of the closed end (14). In one embodiment, the bottom slots (25a, 25b) are defined by the bottom side (13). In one embodiment, the bottom slots (25a, 25b) are defined by the bottom side (13) and are positioned between the apertures (18) and pyramidal protuberances (22) (FIGS. 6B, 7B, 8B) or bristles (23) (FIG. 9B). In one embodiment, the bottom slots (25a, 25b) are oriented substantially parallel to the top slot (19) in order to allow flexing or bending of the article (1) simultaneously at the top slot (19) and the bottom slots (25a, 25b) in a "hinge-like" manner as needed for example, when the tongue is moved upwardly or downwardly towards the teeth. The "hinge-like" top and bottom slots (19, 25a, 25b) thus facilitate the flexibility or bending of the article (1) during use.

In one embodiment, the weakening structure comprises one or more edge slots (27) defined by the edge (15) (FIGS. 7C, 8A, 8B, 9C). In one embodiment, there is at least one edge slot (27). In one embodiment, there are at least two edge slots (27). In one embodiment, there are at least three edge slots (27). In one embodiment, the edge slots (27) are parallel with the top and bottom sides (11, 13). In one embodiment, the edge slots (27) are perpendicular to the top slot (19) and/or bottom slots (25a, 25b). In one embodiment, the edge slots (27) have a length sufficient to span at least from a portion of the apertures (18) to a portion of the pyramidal protuberances (22) or bristles (23) (i.e., the area where the tongue is capable of flexing or bending). The positioning and length of the edge slots (27) allows flexing or bending of the article (1) in a "hinge-like" manner as needed for example, when the tongue is moved upwardly or downwardly towards the teeth. The "hinge-like" edge slots (27) thus facilitate the flexibility or bending of the article (1) during use.

It will be appreciated that various other designs of "hinge-like" weakening structures may be suitable for the article (1). In one embodiment, the weakening structure comprises a hinge, pivot, fold, joint, groove, web, or the like.

In one embodiment, the weakening structure comprises one or more spacings (21) between adjacent pyramidal protuberances (22) or bristles (23) (FIGS. 7A, 7B, 9A, 9B). The pyramidal protuberances (22) or bristles (23) are arranged as closely together as is practicable, while also maintaining the flexibility or bending of the article (1) so as to be maneuverable within the mouth.

In one embodiment, the weakening structure comprises a weakened portion of the article (1). In one embodiment, the weakened portion is provided on one or more of the top side (11), bottom side (13), and edge (15). The weakened portion may be formed by reducing the thickness of the elastomeric material in any area of the top side (11), bottom side (13), and/or edge (15).

It will be appreciated that the article (1) of the present invention is so simple but rugged in construction that it can be made at low cost. The article (1) may be easily fabricated. The article (1) is preferably of one-piece construction, with the pyramidal protuberances (22) or bristles (23) being formed integrally with the closed end (14) so that they do not become dislodged. The article (1) may be formed by dipping, molding, foaming, extrusion, and other processes known in the art. Preferably, the article (1) is formed by dipping or molding. Briefly, dipping involves immersing a former into a compound such as, for example, an elastomer. The coating is then dried using filtered air to prevent atmospheric contamination. After drying, the formers are dipped once more and dried again. On completion of the dipping process, the open end is rolled to form the elastic member (20), and is passed through an oven to vulcanize the compound. A soaking process and high pressure water jets are used to loosen the article (1) from the former, and the article (1) is then dried. Briefly, molding involves shaping the article (1) in a mold, with vulcanization generally conducted simultaneously. Both dipping and molding are relatively simple and rapid processes for producing the article (1).

The article (1) of this invention may be impregnated or coated with a non-toxic substance which is beneficial to the teeth and gums. The substance is preferably compatible with the material(s) of which the article (1) has been formed to avoid degradation or destruction of the article (1) in any manner. Preferably, the substance is soluble in saliva and may be swallowed naturally by the user without having any adverse effect. In one embodiment, the article (1) comprises a coating of a substance on one or both of the body (10) and the protuberances (22) or bristles (23). The coating may be formed or deposited as a thin film on at least a part of the surface of the body (10) and/or the faces of the protuberances (22), or bristles (23). In that respect, the thickness will vary with the particular substance. The thickness will be thin enough that the coating does not interfere with the dimensional tolerances or flexibility of the article (1) for its intended utility. In one embodiment, the coating has a thickness in the range of about 0.1 mm to about 1 mm.

The coating can be a substance including, but not limited to, an antibacterial agent, an antibiotic, an anti-inflammatory agent, a tissue ingrowth promoter, a dentifrice, a tooth whitening agent, a breath freshener, a flavoring, a polishing agent, or combinations thereof. Preferably, a flavoring such as mint, spearmint, wintergreen, cinnamon, strawberry, cherry, bubble gum, citrus, etc. may be used so that the usage of the article (1) will be more pleasant.

The article (1) is preferably sterilized without applying excessive thermal energy, which can melt materials such as, for example, rubber or latex. The sterilized article (1) should be sealed in packaging which excludes direct and indirect sunlight, artificial light with ultraviolet content, and oxygen penetration to avoid deterioration. As an example, the article (1) may be individually packaged flat within a polyester peelable pouch or sachet which is sized to fit within a wallet or pocket, and can thus be conveniently carried and ready for use at all times.

Figure 4:
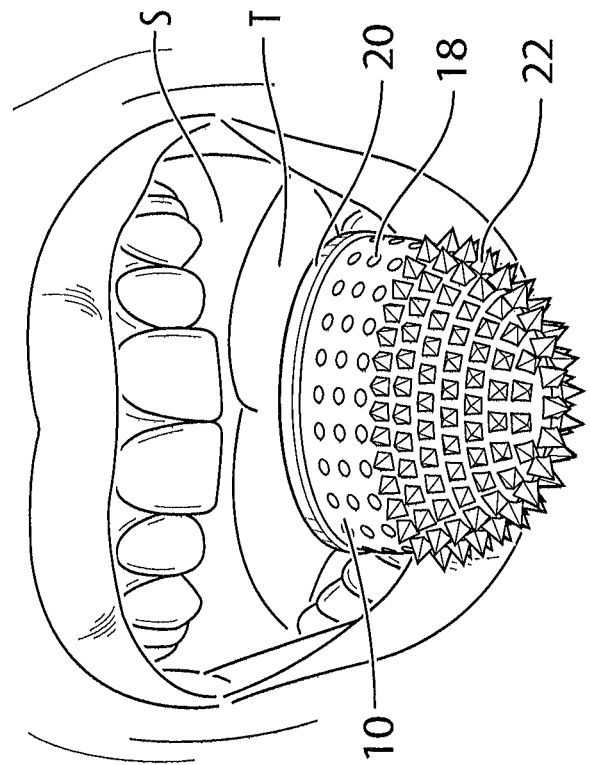
FIG. 4 is a front view of a patient's oral cavity illustrating a natural position of the patient's tongue, with one embodiment of the tongue-mounted cleaning article in use.
Figure 5:
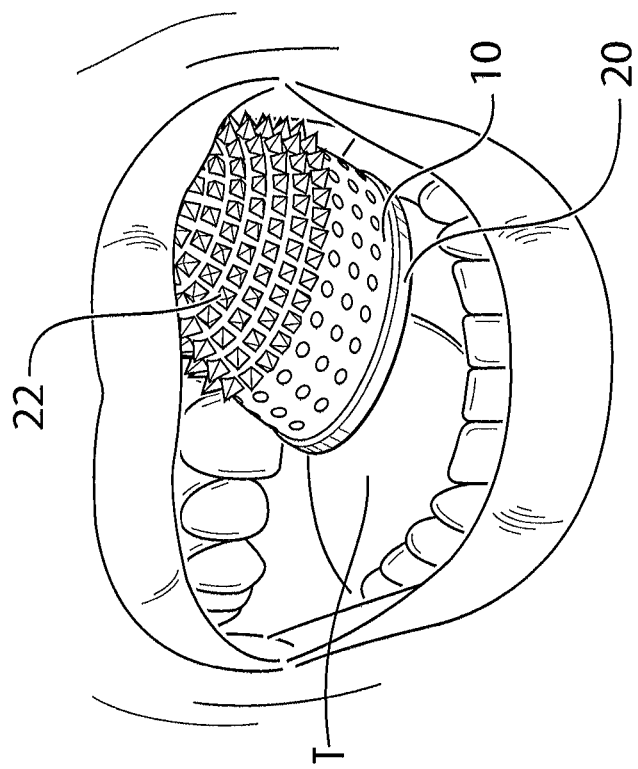
FIG. 5 is a top view of the tongue-mounted cleaning article of FIG. 4.
Figure 7A:
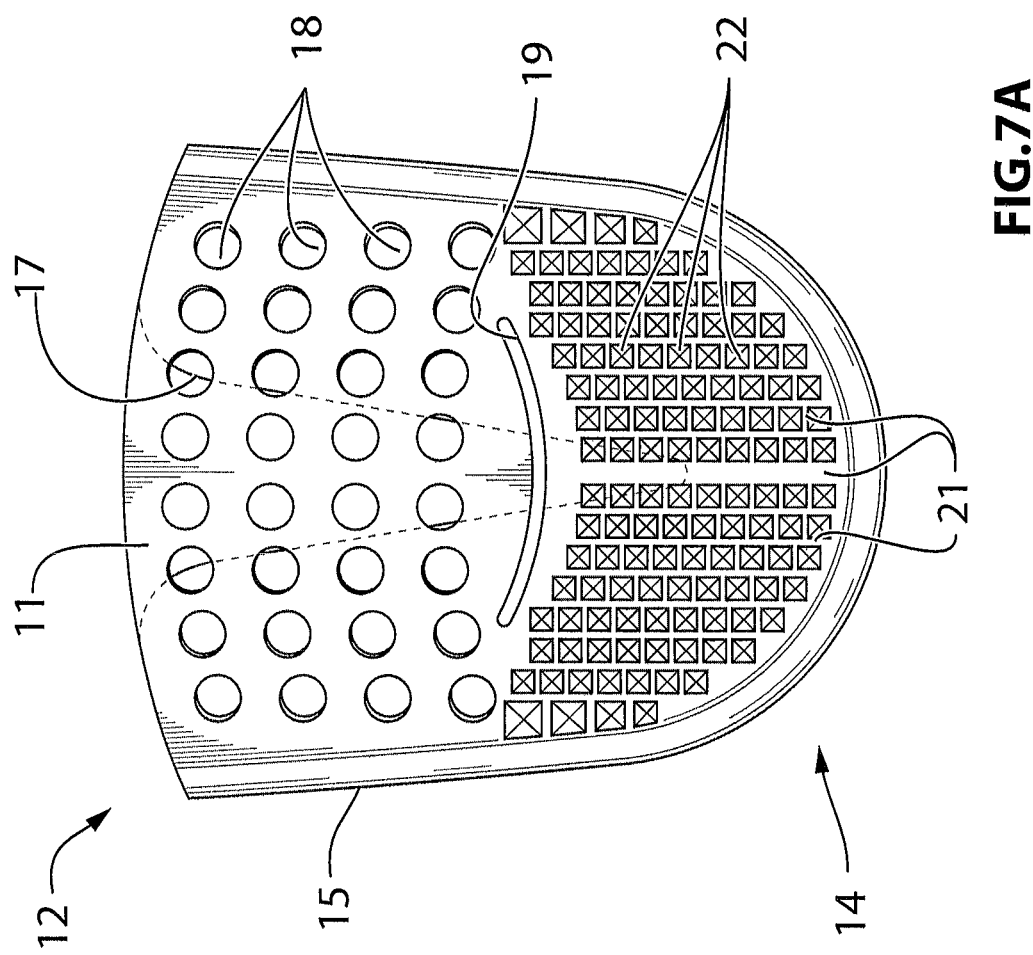
FIG. 7A is a top view of one embodiment of the tongue-mounted cleaning article of the present invention.
Figure 8A:
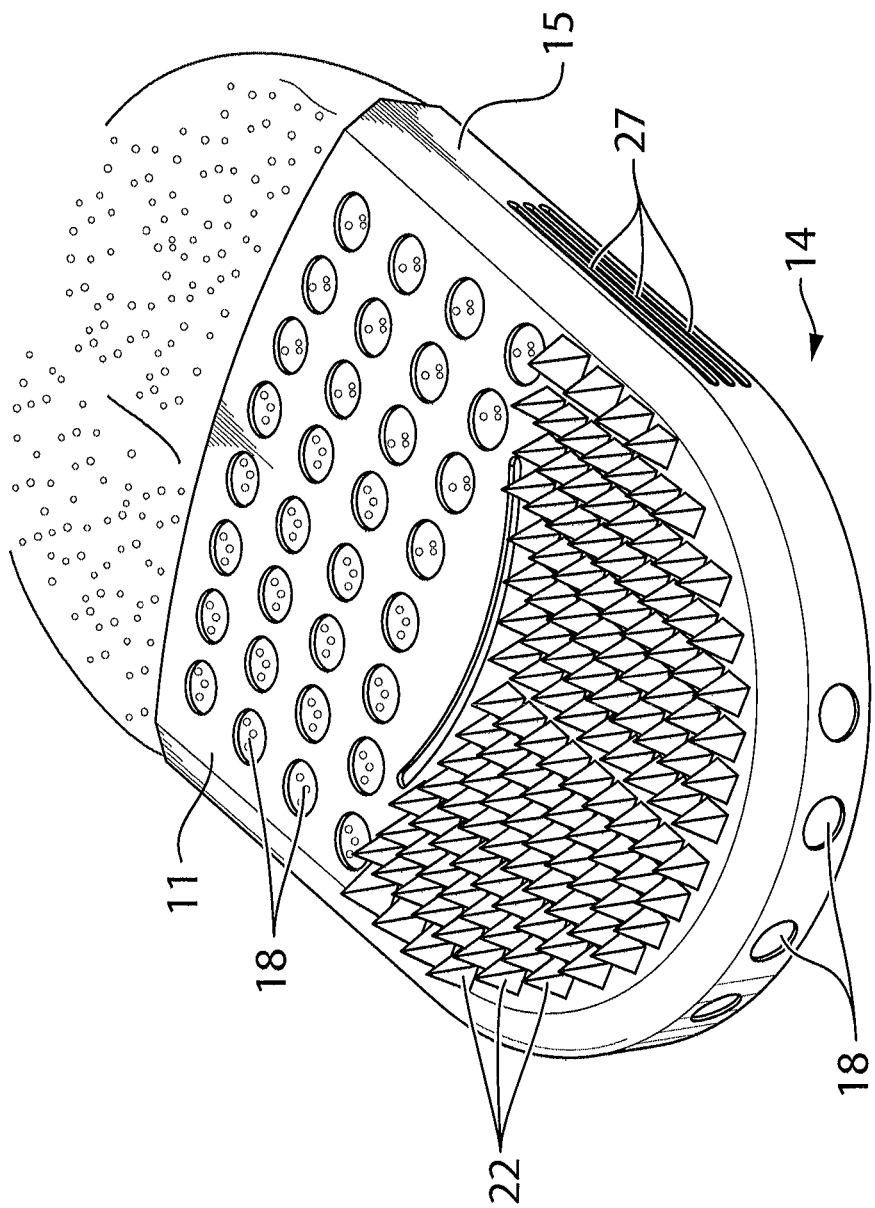
FIG. 8A is a top view of a patient's tongue, with the tongue-mounted cleaning article of FIG. 7A in use.
Figure 8B:
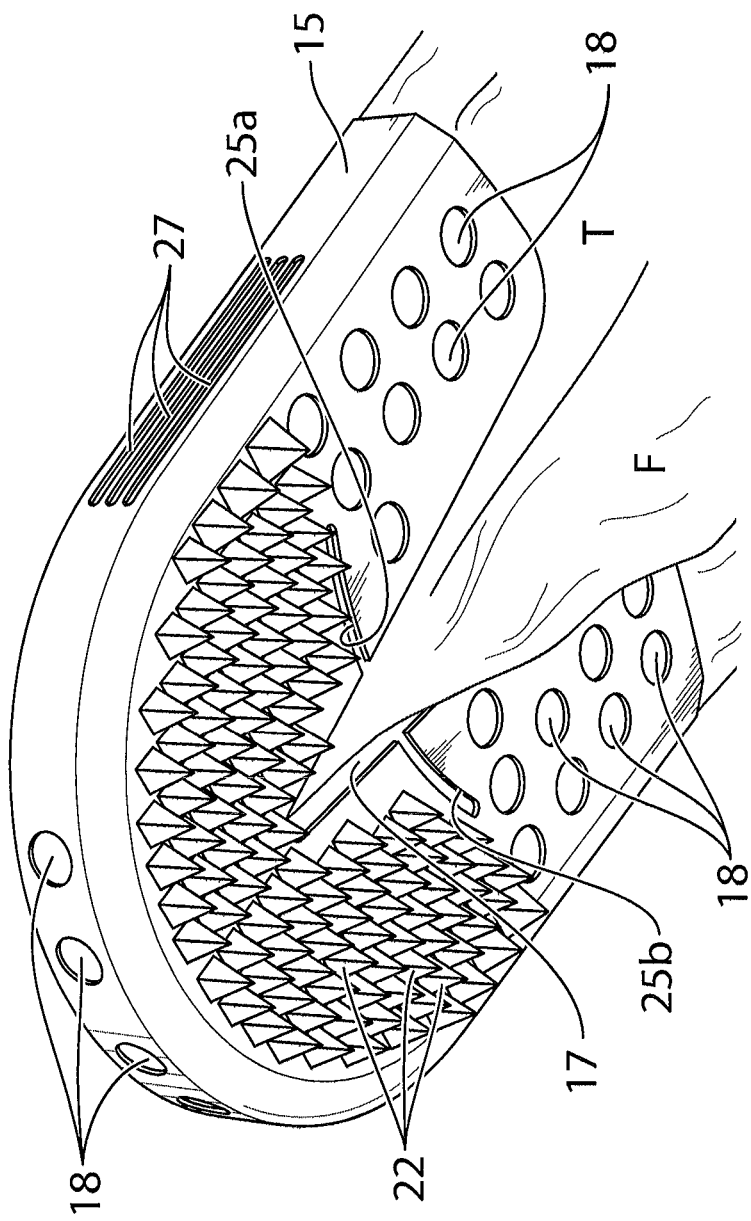
FIG. 8B is a bottom view of a patient's tongue, with the tongue-mounted cleaning article of FIG. 7A in use.

Embodiments of the article (1) in use are shown for example, in FIGS. 4-5 which show the article (1) mounted over the tongue T of a user. FIGS. 4 and 5 illustrate enlarged views of the oral cavity, the tongue T and the soft palate S. To fit the article (1) over the tongue, the elastic member (20) is first stretched with the fingers to allow the tongue to be inserted into the open end (12). The tongue is advanced into the body (10) until the tip of the tongue fits snugly within the closed end (14). The article (1) may be adjusted by the user to cover a greater or lesser portion of the tongue depending upon the desired fit and comfort so long as the covered portion of the tongue is sufficient for the article (1) to be secured over the tongue. The article (1) may be disposed over at least a portion of the tongue, preferably over at least an anterior portion of the tongue. FIG. 8B shows the article (1) disposed over substantially the entirety of the tongue T, with the frenulum F received and accommodated by the centered slot (17).

Once the article (1) is mounted over the tongue, the tongue may be freely maneuvered within the mouth, using the pyramidal protuberances (22) or bristles (23) to remove plaque and debris between the teeth, to scrape and clean the teeth, to massage the gums, and to promote salivary excretion to cleanse the mouth. Manipulation of the article (1) by the tongue thus mimics the brushing action of a toothbrush. In one embodiment, the apices (28) of the pyramidal protuberances (22) are insertable between the teeth to remove plaque and debris, which collects between adjacent pyramidal protuberances (22). The plaque and debris collects along the faces (26) or at the bases (24) of adjacent pyramidal protuberances (22). The apices (28) also contact the gums to provide a massaging action. The article (1) may be used to clean the teeth and gums in any area of the mouth where the tongue may reach. Further, sensitive teeth and gums may be cleaned since the user can easily control the amount of pressure which is applied.

Due to being restrained by the elastomeric material, elastic member (20), and/or the suction of the apertures (18), the article (1) cannot be easily displaced or dislodged except by purposeful removal by the user. To remove the article (1), the user grasps the elastic member (20) with the fingers and rolls the elastic member (20) towards the closed end (14) to remove the article (1) smoothly off the tongue. Alternatively, the user may stretch the elastic member (20) with the fingers to remove it away from both sides of the tongue, and exert sufficient force to pull the article (1) off the tongue. The article (1) can then be disposed since it is designed for single use to avoid accumulation of bacteria which is a common problem with toothbrushes.

The article (1) of the present invention may be used in a variety of circumstances. The article (1) can be used in public since it is discretely inconspicuous within the mouth. Accordingly, the article (1) enables cleaning of the teeth and gums after any meal, during work or social activities, or while in transit or travelling. Since the article (1) operates essentially hands-free other than during attachment or detachment, it conveniently may be used to clean the teeth and gums without halting activity. The article (1) may be made readily available to restaurant or hotel guests, campers, or students. Use of the article (1) is not limited to only active individuals. The article (1) may be useful for elderly, hospital patients, or individuals with physical limitations.

It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

REFERENCES

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

De Oliveira, C.; Watt, R. and Hamer, M. (2010 May 27) Toothbrushing, inflammation, and risk of cardiovascular disease: results from Scottish Health Survey. *BMJ* 340: c2451.

Deshpande, K.; Jain, A.; Sharma, R.; Prashar, S. and Jain, R. (2010 October-December) Diabetes and periodontitis. *J Indian Soc Periodontol.* 14(4): 207-212.

Kelsey, J. L. and Lamster, I. B. (2008 July) Influence of musculoskeletal conditions on oral health among older adults. *Am J Public Health.* 98(7): 1177-1183.

Komiyama, E. Y.; Back-Brito, G. N.; Balducci, I. and Koga-Ito, C. Y. (2010 January-March) Evaluation of alternative methods for the disinfection of toothbrushes. *Braz Oral Res.* 24(1):28-33.

Li, X.; Kolltveit, K. M.; Tronstad, L. and Olsen, I. (2000) Systemic diseases caused by oral infection. *Clinical Microbiology Reviews* 13(4):547-58.

Lockhart, P. B.; Brennan, M. T.; Thornhill, M.; Michalowicz, B. S.; Noll, J.; Bahrani-Mougeot, F. K. and Sasser, H. C. (2009 October) Poor oral hygiene as a risk factor for infective endocarditis-related bacteremia. *J Am Dent Assoc.* 140 (10):1238-44.

Lowenthal, A. and Lowenthal, M. N. (2001 September) Gingival hypertrophy due to drugs. *Isr Med Assoc J.* 3(9):705.

Michalowicz, B. S.; Hodges, J. S.; DiAngelis, A. J.; Lupo, V. R.; Novak, M. J.; Ferguson, J. E.; Buchanan, W.; Bofill, J.; Papapanou, P. N.; Mitchell, D. A.; Matseoane, S.; Tschida, P. A. and OPT Study. (2006 Nov. 2) Treatment of periodontal disease and the risk of preterm birth, *N Engl J. Med.* 355(18):1885-94.

Raghavendran, K.; Mylotte, J. M. and Scannapieco, F. A. (2007) Nursing home-associated pneumonia, hospital-acquired pneumonia and ventilator-associated pneumonia: the contribution of dental biofilms and periodontal inflammation. *Periodontol* 2000 44:164-77, Rawls, H. R.; Mkwayi-Tulloch, N. J.; Casella, R. and Cosgrove, R. (1989 December) The measurement of toothbrush wear. *J. Dent Res.* 68(12):1781-5.

Sato, S.; Ito, I. Y.; Lara, E. H.; Panzeri, H.; Albuquerque Jr., R. F. and Pedrazzi, V. (2004 June) Bacterial survival rate on toothbrushes and their decontamination with antimicrobial solutions. *J Appl Oral Sci.* 12(2):99-103.

Spahr, A.; Klein, E.; Khuseyinova, N.; Boeckh, C.; Muche, R.; Kunze, M.; Rothenbacher, D.; Pezeshki, G.; Hoffmeister, A. and Koenig, W. (2006 Mar. 13) Periodontal infections and coronary heart disease: role of periodontal bacteria and importance of total pathogen burden in the Coronary Event and Periodontal Disease (CORODONT) study. *Arch Intern Med.* 166(5):554-9.

What is claimed is:

1. A tongue-mounted cleaning article for caring for the teeth and gums comprising:
   a) an elongated body comprising a top side, a bottom side, and an edge, and defining an inner cavity formed in the configuration of the tongue for receiving and accommodating the tongue, a slot for receiving and accommodating the frenulum on the undersurface of the tongue, a plurality of apertures therethrough positioned on at least the top side and the bottom side, and one or more weakening structures positioned on one or more of the top side, the bottom side, or the edge;
   b) an open end sized to permit insertion of tongue; and
   c) a closed end being narrower than the open end and configured in the shape of the tip of the tongue, the closed end comprising a plurality of pyramidal protuberances or bristles disposed over a portion or entirety of its surface, wherein the pyramidal protuberances or bristles project outwardly for cleaning the teeth and gums by appropriate movement of the tongue.

2. The article of claim 1, wherein at least one aperture is positioned on the edge at the tip of the closed end.

3. The article of claim 1, wherein the weakening structure comprises one or more top slots defined by the top side.

4. The article of claim 1, wherein the weakening structure comprises one or more pairs of bottom slots defined by the bottom side.

5. The article of claim 1, wherein the weakening structure comprises one or more edge slots defined by the edge.

6. The article of claim 1, wherein the weakening structure comprises one or more spacings between adjacent pyramidal protuberances or bristles.

7. The article of claim 1, wherein each pyramidal protuberance comprises a polygonal base and a plurality of triangular faces which converge at an apex, the bases of the faces of each pyramidal protuberance directly abutting the bases of the faces of adjacent pyramidal protuberances to define channels between the protuberances.

8. The article of claim 7, wherein each pyramidal protuberance comprises at least three triangular faces.

9. The article of claim 8, wherein each pyramidal protuberance comprises four triangular faces.

10. The article of claim 7, wherein one or more abrasive pads are provided on one or more of the triangular faces.

11. The article of claim 1, comprising an elastomer.

12. The article of claim 1, further comprising a coating on one or both of the body and the protuberances or the bristles, the coating being at least one of antibacterial agent, an antibiotic, an anti-inflammatory agent, a tissue ingrowth promoter, a dentifrice, a tooth whitening agent, a breath freshener, a flavoring, a polishing agent, or combinations thereof.

13. A method of cleaning the teeth and gums by appropriate movement of the tongue, the method comprising the steps of: providing the article of claim 1; mounting the article on the tongue; and manipulating the article with the tongue to allow the pyramidal protuberances or bristles to clean the teeth and gums.

* * * * *